(12) United States Patent
Salaita et al.

(10) Patent No.: US 10,900,069 B2
(45) Date of Patent: Jan. 26, 2021

(54) DEVICES AND METHODS USEFUL FOR DETECTING MECHANICAL FORCES OF LIGAND RECEPTOR INTERACTIONS

(71) Applicant: Emory University, Atlanta, GA (US)

(72) Inventors: Khalid Salaita, Decatur, GA (US); Pui-yan Ma, Atlanta, GA (US)

(73) Assignee: Emory University, Atlanta, GA (US)

( * ) Notice: Subject to any disclaimer, the term of this patent is extended or adjusted under 35 U.S.C. 154(b) by 254 days.

(21) Appl. No.: 15/456,024

(22) Filed: Mar. 10, 2017

(65) Prior Publication Data

US 2017/0260575 A1 Sep. 14, 2017

Related U.S. Application Data

(60) Provisional application No. 62/306,348, filed on Mar. 10, 2016.

(51) Int. Cl.
| | |
|---|---|
| *C12P 19/34* | (2006.01) |
| *C12Q 1/6816* | (2018.01) |
| *C12Q 1/6848* | (2018.01) |
| *C12Q 1/6809* | (2018.01) |
| *C12Q 1/6844* | (2018.01) |
| *C12Q 1/28* | (2006.01) |
| *G01N 33/542* | (2006.01) |

(52) U.S. Cl.
CPC .......... *C12Q 1/6816* (2013.01); *C12Q 1/28* (2013.01); *C12Q 1/6809* (2013.01); *C12Q 1/6844* (2013.01); *C12Q 1/6848* (2013.01); *C12Y 111/01007* (2013.01); *G01N 33/542* (2013.01); *G01N 2458/10* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS

| | | |
|---|---|---|
| 8,647,590 B2 | 2/2014 | Brennen |
| 9,423,234 B2 | 8/2016 | Rowat |

(Continued)

FOREIGN PATENT DOCUMENTS

WO 2016083779 6/2016

OTHER PUBLICATIONS

Brockman et al. Mapping the 3D orientation of piconewton integrin traction forces, Nat Methods. 2018, 15 (2):115-118.

(Continued)

*Primary Examiner* — Frank W Lu
(74) *Attorney, Agent, or Firm* — Emory Patent Group

(57) ABSTRACT

This disclosure related to methods of detecting mechanical forces required to separate ligand and receptor interactions. In certain embodiments, this disclosure relates to methods of detecting mechanical forces between a ligand and receptor, where the ligand is immobilized on a surface using weaker forces. Ligand-receptor forces lead to dissociation of the ligand that can be detected and amplified. In certain embodiments, the disclosure relates to methods of detecting ligand and receptor interactions comprising linking a ligand to one of two binding partners, wherein the binding partners have attracting forces that are less than the forces between the ligand and a receptor of the ligand such that when the ligand binds the receptor, the binding partners will separate. Separation of the binding partners can be detected.

6 Claims, 10 Drawing Sheets

Specification includes a Sequence Listing.

(56) References Cited

U.S. PATENT DOCUMENTS

| | | |
|---|---|---|
| 2009/0176253 A1 | 7/2009 | Bieniarz |
| 2009/0227043 A1 | 9/2009 | Huang |
| 2009/0263850 A1 | 10/2009 | Liulevych |
| 2014/0336071 A1 | 11/2014 | Salaita |

OTHER PUBLICATIONS

Chang et al. A General Approach for Generating Fluorescent Probes to Visualize Piconewton Forces at the Cell Surface, J Am Chem Soc. 2016, 138(9):2901-4.

Galior et al. Titin-Based Nanoparticle Tension Sensors Map High-Magnitude Integrin Forces within Focal Adhesions, Nano Lett. 2016, 16, 341-348.

Jurchenko et al. Integrin-Generated Forces Lead to Streptavidin-Biotin Unbinding in Cellular Adhesions, Biophysical Journal, 2014, 106, 1436-1446.

Koussa et al. DNA Nanoswitches: A quantitative platform for gel-based biomolecular interaction analysis, Nat Methods. 2015, 12(2): 123-126.

Liu et al. Tension Sensing Nanoparticles for Mechano-Imaging at the Living/ Nonliving Interface, J Am Chem Soc. 2013, 135(14):5320-3.

Liu et al. Nanoparticle Tension Probes Patterned at the Nanoscale: Impact of Integrin Clustering on Force Transmission, Nano Lett. 2014, 14(10):5539-46.

Lui et al. DNA-based nanoparticle tension sensors reveal that T-cell receptors transmit defined pN forces to their antigens for enhanced fidelity, Proc Natl Acad Sci U S A, 2016, 113 (20) 5610-5615.

Ma et al. The Mechanically-induced Catalytic Amplification Reaction for Readout of Receptor-Mediated Cellular Forces, Angew Chem Int Ed Engl. 2016, 55(18): 5488-5492.

Moraes et al. Microfabricated arrays for high-throughput screening of cellular response to cyclic substrate deformation, Lab Chip. 2010, 10(2):227-34.

Park et al. High-throughput screening for modulators of cellular contractile force,Integr Biol (Camb). 2015, 7(10): 1318-1324.

Salaita et al. Restriction of Receptor Movement Alters Cellular Response: Physical Force Sensing by EphA2, Science. 2010, 327(5971):1380-5.

Salaita et al. Restriction of Receptor Movement Alters Cellular Response: Physical Force Sensing by EphA2, Science. 2010, 327(5971):1380-5, Supplemental Material.

Stabley et al. Visualizing mechanical tension across membrane receptors with a fluorescent sensor, Nat Methods. 2011, 9(1):64-7.

Wang et al. Defining Single Molecular Forces Required to Activate Integrin and Notch Signaling, Science. 2013, 340 (6135): 991-994.

Zhang et al. DNA-based digital tension probes reveal integrin forces during early cell adhesion, Nat Commun.2015, 5: 5167.

Zhang et al. Platelet integrins exhibit anisotropic mechanosensing and harness piconewton forces to mediate platelet aggregation, Proc Natl Acad Sci U S A. 2018, 115(2):325-330.

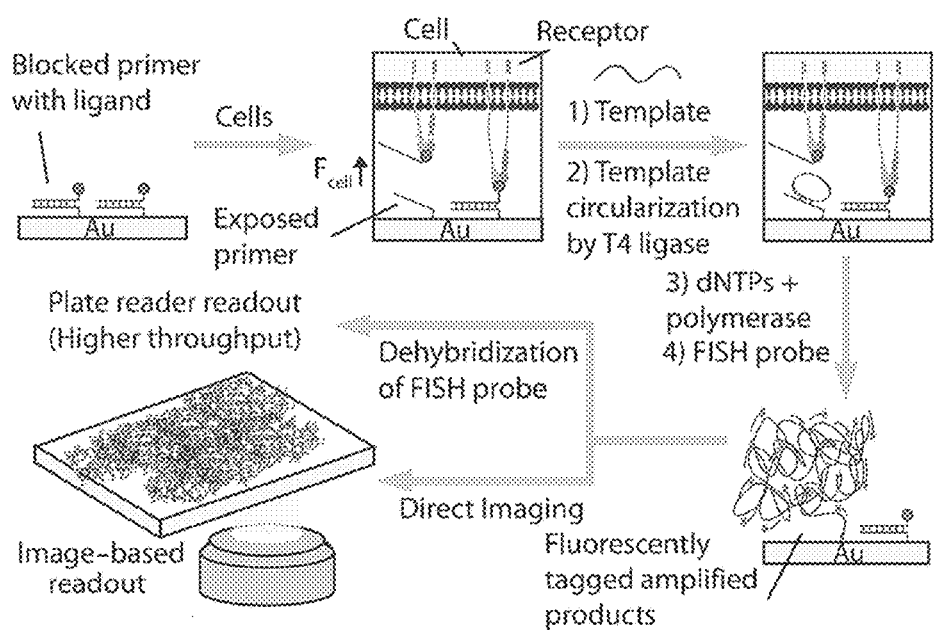
FIG. 1
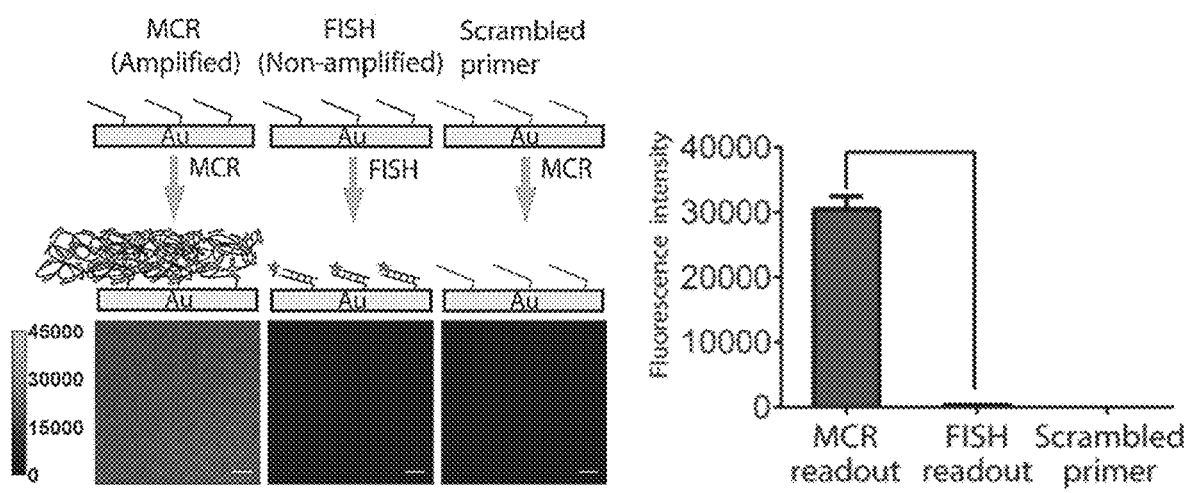
FIG. 2A
FIG. 2B

DEVICES AND METHODS USEFUL FOR DETECTING MECHANICAL FORCES OF LIGAND RECEPTOR INTERACTIONS

CROSS REFERENCE TO RELATED APPLICATIONS

This application claims the benefit of U.S. Provisional Application No. 62/306,348 filed Mar. 10, 2016. The entirety of this application is hereby incorporated by reference for all purposes.

STATEMENT REGARDING FEDERALLY SPONSORED RESEARCH

This invention was made with government support under R01-GM097399 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 16085US_ST25.txt. The text file is 2 KB, was created on Mar. 10, 2017, and is being submitted electronically via EFS-Web.

BACKGROUND

Mechanics play a fundamental role in cell biology, but detecting piconewton forces is challenging due to the lack of accessible and high throughput assays. Current assays for the measurement of receptor-mediated forces in cells require expensive high-end microscopy systems with single-photon counting EMCCDs coupled with high-numerical aperture (NA) objectives to detect changes in energy transfer efficiency. Therefore, high throughput screening of drugs that target mechanical processes and screening the mechanical phenotype of a library of cells is expensive and a challenge. Therefore, there is a need to develop strategies that transduce pN forces into an easily quantifiable, and amplified chemical signal amenable to high-throughput screening of cells.

Park et al. report high-throughput screening for modulators of cellular contractile force. Integr Biol, 2015, 7(10): 1318-24. Koussa et al. report DNA nanoswitches as a quantitative platform for gel-based biomolecular interaction analysis. Nat Methods, 2015, 12(2):123-6. Wang et al. report molecular forces required to activate integrin and notch signaling. Science, 2013, 340(6135): 991-994.

See also WO 2016/083779, U.S. Patent Application Publications 2009/0263850 and 2014/0336071, and U.S. Pat. Nos. 9,423,234 and 8,647,590, Jurchenko et al. Biophys J., 2014, 106(7): 1436-1446 and Ma et al. Angew Chem Int Ed Engl, 2016, 55(18):5488-92.

References cited herein are not an admission of prior art.

SUMMARY

This disclosure related to methods of detecting mechanical forces required to separate ligand and receptor interactions. In certain embodiments, this disclosure relates to methods of detecting mechanical forces between a ligand and receptor, where the ligand is immobilized on a surface using weaker forces. Ligand-receptor forces lead to dissociation of the ligand that can be detected and amplified. In certain embodiments, the disclosure relates to methods of detecting ligand and receptor interactions comprising linking a ligand to one of two binding partners, wherein the binding partners have attracting forces that are less than the forces between the ligand and a receptor of the ligand such that when the ligand binds the receptor, the binding partners will separate. Separation of the binding partners can be detected.

In certain embodiments, the receptor is within or on the surface of a cell membrane, phospholipid bilayer membrane, or micelle. In certain embodiments, the binding partners are hydrogen binding partners. In certain embodiments, the binding partners are a pair of single stranded nucleic acids that can hybridize with each other.

In certain embodiments, the disclosure contemplates methods disclosed herein that can be used to amplify non-cell generated forces such as measure shear forces in a device or in a viscous solution.

In certain embodiments, the existence of the separated binding partner is detected through amplification techniques. In one example, double stranded nucleic acids are separated providing a free single stranded nucleic acid. The free single strand can be detected with another hybridizing strand, probe, or other detection conjugates.

In certain embodiments, the detection conjugate is a second single stranded nucleic acids with terminal bases configured to hybridize with the free single strand to form a circular construct that can be amplified by rolling circle amplification, e.g., by exposure to nucleotides and phi29 polymerase.

In certain embodiments, the detection conjugate may be single stranded nucleic acid conjugated to an enzyme such as horseradish peroxidase enzyme (HRP) that can catalyze a reaction capable of producing a light signal, e.g., HRP catalyzes the conversion of chromogenic substrates (e.g., TMB, DAB, ABTS) into colored products, and produces light when acting on chemiluminescent substrates. In other embodiments, the HRP can be used to tag a cell with biotin groups that can be detected by fluorescence or mass spectrometry.

In certain embodiments, contemplated binder partners maybe an antibody and epitope peptide.

In certain embodiments, the disclosure also contemplates methods of exposing systems disclosed herein to molecules, drugs, or test molecules in order to identify or quantify the interference of ligand receptor interactions.

In certain embodiments, this disclosure relates to device comprising: a) a surface, b) a first binding partner linked to an area the surface, c) a second binder partner configured to bind with the first binding partner, and d) a ligand linked to the second binding partner. In certain embodiments, the device is in contact with cells that contain receptors to the ligand. In certain embodiments, the device comprises a cell in contact with the area of the surface.

In certain embodiments, this disclosure relates to device comprising: a) a surface, b) a first binding partner linked to an area the surface, c) a second binder partner configured to bind with the first binding partner, and d) a receptor linked to the second binding partner. In certain embodiments, the device is in contact with cells that contain ligands to the receptor. In certain embodiments, the device comprises a cell in contact with the area of the surface.

In certain embodiments, the ligand comprises a polysaccharide, peptide, glycopeptide, or steroid. In certain embodiments, the ligand comprises a polypeptide of three or more amino acids. In certain embodiments, the ligand comprises a polypeptide of four or more amino acids. In certain embodiments, the ligand comprises a polypeptide of ten or more amino acids.

In certain embodiments, the receptor comprises a polypeptide of ten or more amino acids. In certain embodiments, the receptor comprises a polypeptide of twenty or more amino acids. In certain embodiments, the receptor is wherein the ligand comprises a polypeptide of forty or more amino acids.

In certain embodiments, the surface contains gold particles and the first binding partner is immobilized to the gold particle through a thiol containing group.

In certain embodiments, the disclosure contemplates arrays comprising a plurality of areas wherein two or more areas contain two or more ligands wherein the ligands are not the same molecules.

In certain embodiments, the disclosure contemplates arrays comprising a plurality of areas wherein two or more areas contain two or more receptors wherein the receptors are not the same molecules.

In certain embodiments, this disclosure relates to device comprising: a) a surface, b) a first strand of a nucleobase polymer linked to an area the surface, c) a second strand of a nucleobase polymer configured to hybridize with the first strand, and d) a ligand linked to the second strand. In certain embodiments, the first strand and second strand are not covalently attached to each other. In certain embodiments, the surface comprises more than two areas and the ligands in the two areas are not the same molecule.

In certain embodiments, this disclosure relates to device comprising: a) a surface, b) a first strand of a nucleobase polymer linked to an area the surface, c) a second strand of a nucleobase polymer configured to hybridize with the first strand, and d) a receptor linked to the second strand. In certain embodiments, the first strand and second strand are not covalently attached to each other. In certain embodiments, the surface comprises more than two areas and the receptors in the two areas are not the same molecule.

In certain embodiments, the device is a transparent, semi-transparent, or opaque, polymer, glass, metal, bead, particle, slide, or array. In certain embodiments, the device is a flat surface comprising gold nanoparticles wherein the first strand of nucleobase polymer is linked to the gold nanoparticles.

In certain embodiments, this disclosure relates to methods of identifying receptor binding to a ligand comprising: mixing 1) a device comprising: a) a surface, b) a first strand of a nucleobase polymer linked to an area of the surface, c) a second strand of a nucleobase polymer configured to hybridize with the first strand and is hybridized with the first strand, and d) a ligand linked to the second strand, and 2) a receptor to the ligand or a cell comprising a receptor to the ligand under conditions such that the receptor binds the ligand; exposing the device to a cells comprising a receptor of the ligand or removing the receptor or the cell from the surface of the device under conditions such that the first strand no longer hybridizes to the second strand providing a first single stranded nucleobase polymer in the area of the surface; using the first single stranded polymer as a primer to isothermally amplify circular DNA providing amplified DNA; and detecting the amplified DNA as an indicator of receptor binding to a ligand.

In certain embodiments, this disclosure relates to methods of identifying ligand binding to a receptor comprising: mixing 1) a device comprising: a) a surface, b) a first strand of a nucleobase polymer linked to an area of the surface, c) a second strand of a nucleobase polymer configured to hybridize with the first strand and is hybridized with the first strand, and d) a receptor linked to the second strand, and 2) a ligand to the receptor or a cell comprising a ligand to the receptor under conditions such that the ligand binds the receptor; exposing the device to a cells comprising a ligand of the receptor or removing the ligand or the cell from the surface of the device under conditions such that the first strand no longer hybridizes to the second strand providing a first single stranded nucleobase polymer in the area of the surface; using the first single stranded polymer as a primer to isothermally amplify circular DNA providing amplified DNA; and detecting the amplified DNA as an indicator of receptor binding to a ligand.

In certain embodiments, this disclosure relates to methods of identifying receptor binding to a ligand comprising; mixing 1) a device comprising: a) a surface, b) a first strand of a nucleobase polymer linked to an area of the surface, c) a second strand of a nucleobase polymer configured to hybridize with the first strand and is hybridized with the first strand, and d) a ligand linked to the second strand, and 2) a cell comprising a receptor to the ligand under conditions such that the receptor binds the ligand under conditions such that the first strand no longer hybridizes to the second strand providing a first single stranded nucleobase polymer in the area of the surface; or a receptor to the ligand or a cell comprising a receptor to the ligand under conditions such that the receptor binds the ligand and removing the receptor or the cell from the surface of the device under conditions such that the first strand no longer hybridizes to the second strand providing a first single stranded nucleobase polymer in the area of the surface; mixing the first single stranded nucleobase polymer with a nucleotides, a polymerase, and a nucleic acid, wherein the nucleic acid comprises a first sequence and second sequence, wherein the first sequence is configured to hybridize to the first single stranded nucleobase polymer, wherein mixing is under conditions such that the second sequence of the nucleic acid is amplified, providing amplified nucleic acids in the area of the surface; mixing the amplified nucleic acids with a probe that binds the amplified nucleic acids, wherein the probe is linked to a reporter molecule; and identifying the reporter molecule in the area of the surface indicating that the ligand is bound to the receptor.

In certain embodiments, the disclosure relates to methods of identifying receptor binding to a ligand comprising; mixing 1) a device comprising: a) a surface, b) a first strand of a nucleobase polymer linked to an area of the surface, c) a second strand of a nucleobase polymer configured to hybridize with the first strand and is hybridized with the first strand, and d) a ligand linked to the second strand; and 2) a receptor to the ligand under conditions such that the receptor binds the ligand under conditions such that the first strand no longer hybridizes to the second strand providing a first single stranded nucleobase polymer in the area of the surface; mixing the first single stranded nucleobase polymer in the area of the surface with a third strand of a nucleobase polymer configured to hybridize with the first strand, under conditions such that the third strand and is hybridized with the first strand; wherein the third strand is conjugated to a catalytic enzyme; mixing the third strand is conjugated to a catalytic enzyme with a substrate to the enzyme such that the enzyme modifies the substrate, providing a modified substrate; and detecting the modified substrate as an indicator of receptor binding to the ligand. In certain embodiments, the enzyme catalyzes the conversion of substrates into colored, fluorescent or phosphorescent modified substrates.

In certain embodiments, the disclosure relates to methods of identifying ligand binding to a receptor comprising; mixing 1) a device comprising: a) a surface, b) a first strand of a nucleobase polymer linked to an area of the surface, c) a second strand of a nucleobase polymer configured to hybridize with the first strand and is hybridized with the first strand, and d) a receptor linked to the second strand; and 2) a ligand to the receptor under conditions such that the ligand binds the receptor under conditions such that the first strand no longer hybridizes to the second strand providing a first single stranded nucleobase polymer in the area of the surface; mixing the first single stranded nucleobase polymer in the area of the surface with a third strand of a nucleobase polymer configured to hybridize with the first strand, under conditions such that the third strand and is hybridized with the first strand; wherein the third strand is conjugated to a catalytic enzyme; mixing the third strand conjugated to a catalytic enzyme with a substrate to the enzyme such that the enzyme modifies the substrate, providing a modified substrate; and detecting the modified substrate as an indicator of ligand binding to the receptor. In certain embodiments, the enzyme catalyzes the conversion of substrates into colored, fluorescent or phosphorescent modified substrates.

In certain embodiments, this disclosure relates to methods of identifying ligand binding to a receptor comprising; mixing 1) a device comprising: a) a surface, b) a first strand of a nucleobase polymer linked to an area of the surface, c) a second strand of a nucleobase polymer configured to hybridize with the first strand and is hybridized with the first strand, and d) a receptor linked to the second strand, and 2) a cell comprising a ligand to the receptor under conditions such that the ligand binds the receptor under conditions such that the first strand no longer hybridizes to the second strand providing a first single stranded nucleobase polymer in the area of the surface; or a ligand to the receptor or a cell comprising a ligand to the receptor under conditions such that the ligand binds the receptor and removing the ligand or the cell from the surface of the device under conditions such that the first strand no longer hybridizes to the second strand providing a first single stranded nucleobase polymer in the area of the surface; mixing the first single stranded nucleobase polymer with a nucleotides, a polymerase, and a nucleic acid, wherein the nucleic acid comprises a first sequence and second sequence, wherein the first sequence is configured to hybridize to the first single stranded nucleobase polymer, wherein mixing is under conditions such that the second sequence of the nucleic acid is amplified, providing amplified nucleic acids in the area of the surface; mixing the amplified nucleic acids with a probe that binds the amplified nucleic acids, wherein the probe is linked to a reporter molecule; and identifying the reporter molecule in the area of the surface indicating that the receptor is bound to the ligand.

In certain embodiments, the probe nucleic acid sequence configured to hybridize to the amplified nucleic acid. In certain embodiments, the probe nucleic acid sequence is contained within the second sequence. In certain embodiments, the reporter molecule is a fluorescent molecule. In certain embodiments, the identifying the reporter molecule in the area of the surface is by imaging the fluorescent molecule in the area.

In certain embodiments, this disclosure contemplates methods of determining that a test compound does inhibit the binding of ligand to a receptor comprising: mixing 1) a test compound with 2) a device comprising: a) a surface, b) a first strand of a nucleobase polymer linked to an area of the surface, c) a second strand of a nucleobase polymer configured to hybridize with the first strand and is hybridized with the first strand, and d) a ligand linked to the second strand, and 3) receptor or a cell comprising a receptor to the ligand under conditions such that the receptor binds the ligand unless the test compound inhibits the binding of the ligand to the receptor and under conditions such that if the receptor is binding the ligand, then the first strand no longer hybridizes to the second strand providing a first single stranded nucleobase polymer in the area of the surface; or optionally removing the receptor or cell from the surface of the device under conditions such that if the receptor is binding the ligand, then the first strand no longer hybridizes to the second strand providing a first single stranded nucleobase polymer in the area of the surface; mixing the area with a nucleotides, a polymerase, and a nucleic acid, wherein the nucleic acid comprising a first sequence and second sequence, wherein the first sequence is configured to hybridize to the first single stranded nucleobase polymer, wherein mixing is under conditions such that if the receptor is binding the ligand the second sequence of the nucleic acid is amplified, providing amplified nucleic acids in the area of the surface and mixing the amplified nucleic acids with a probe that binds the amplified nucleic acids, wherein the probe is linked to a reporter molecule; and identifying the absence of the reporter molecule in the area of the surface indicating that the ligand did not bind to the receptor and indicating that the test compound inhibits the binding of the ligand to the receptor.

In certain embodiments, this disclosure contemplates methods of determining that a test compound does inhibit the binding of receptor to a ligand comprising: mixing 1) a test compound with 2) a device comprising: a) a surface, b) a first strand of a nucleobase polymer linked to an area of the surface, c) a second strand of a nucleobase polymer configured to hybridize with the first strand and is hybridized with the first strand, and d) a receptor linked to the second strand, and 3) ligand or a cell comprising a ligand to the receptor under conditions such that the ligand binds the receptor unless the test compound inhibits the binding of the receptor to the ligand and under conditions such that if the ligand is binding the receptor, then the first strand no longer hybridizes to the second strand providing a first single stranded nucleobase polymer in the area of the surface; or optionally removing the receptor or cell from the surface of the device under conditions such that if the ligand is binding the receptor, then the first strand no longer hybridizes to the second strand providing a first single stranded nucleobase polymer in the area of the surface; mixing the area with a nucleotides, a polymerase, and a nucleic acid, wherein the nucleic acid comprising a first sequence and second sequence, wherein the first sequence is configured to hybridize to the first single stranded nucleobase polymer, wherein mixing is under conditions such that if the ligand is binding the receptor the second sequence of the nucleic acid is amplified, providing amplified nucleic acids in the area of the surface and mixing the amplified nucleic acids with a probe that binds the amplified nucleic acids, wherein the probe is linked to a reporter molecule; and identifying the absence of the reporter molecule in the area of the surface indicating that the receptor did not bind to the ligand and indicating that the test compound inhibits the binding of the receptor to the ligand.

In certain embodiments, the disclosure contemplates methods of determining that a test compound does not inhibit the binding of ligand to a receptor comprising: mixing 1) a test compound and 2) a device comprising: a) a surface, b) a first strand of a nucleobase polymer linked to an area of the surface, c) a second strand of a nucleobase polymer configured to hybridize with the first strand and is hybridized with the first strand, and d) a ligand linked to the second strand, and 3) receptor or a cell comprising a receptor to the ligand under conditions such that the receptor binds the ligand unless the test compound inhibits the binding of the ligand to the receptor and under conditions such that if the receptor is binding the ligand, then the first strand no longer hybridizes to the second strand providing a first single stranded nucleobase polymer in the area of the surface; or optionally removing the receptor or the cell from the surface of the device under conditions such that if the receptor is binding the ligand, then the first strand no longer hybridizes to the second strand providing a first single stranded nucleobase polymer in the area of the surface; mixing the first single stranded nucleobase polymer with a nucleotides, a polymerase, and a nucleic acid, wherein the nucleic acid comprising a first sequence and second sequence, wherein the first sequence is configured to hybridize to the first single stranded nucleobase polymer, wherein mixing is under conditions such that the second sequence of the nucleic acid is amplified, providing amplified nucleic acids in the area of the surface; mixing the amplified nucleic acids with a probe that binds the amplified nucleic acids, wherein the probe is linked to a reporter molecule; and identifying the reporter molecule in the area of the surface indicating that the ligand is bound to the receptor and indicating that the test compound does not inhibit the binding of the ligand to the receptor.

In certain embodiments, this disclosure contemplates methods of determining that a test compound does inhibit the binding of receptor to a ligand comprising: mixing 1) a test compound with 2) a device comprising: a) a surface, b) a first strand of a nucleobase polymer linked to an area of the surface, c) a second strand of a nucleobase polymer configured to hybridize with the first strand and is hybridized with the first strand, and d) a receptor linked to the second strand, and 3) ligand or a cell comprising a ligand to the receptor under conditions such that the ligand binds the receptor unless the test compound inhibits the binding of the receptor to the ligand and under conditions such that if the ligand is binding the receptor, then the first strand no longer hybridizes to the second strand providing a first single stranded nucleobase polymer in the area of the surface; or optionally removing the ligand or cell from the surface of the device under conditions such that if the ligand is binding the receptor, then the first strand no longer hybridizes to the second strand providing a first single stranded nucleobase polymer in the area of the surface; mixing the area with a nucleotides, a polymerase, and a nucleic acid, wherein the nucleic acid comprising a first sequence and second sequence, wherein the first sequence is configured to hybridize to the first single stranded nucleobase polymer, wherein mixing is under conditions such that if the ligand is binding the receptor the second sequence of the nucleic acid is amplified, providing amplified nucleic acids in the area of the surface and mixing the amplified nucleic acids with a probe that binds the amplified nucleic acids, wherein the probe is linked to a reporter molecule; and identifying the absence of the reporter molecule in the area of the surface indicating that the receptor did not bind to the ligand and indicating that the test compound inhibits the binding of the receptor to the ligand.

BRIEF DESCRIPTION OF THE DRAWINGS

FIG. 1 illustrates a mechanically induced catalytic amplification reaction.

FIG. 2A shows a schematic and corresponding epifluorescence images.

FIG. 2B shows a plot of mean signal from positive (primer), and negative controls (non-amplified sample, and scrambled primer). The data indicates selectivity and efficiency of surface initiated isothermal amplification.)

DETAILED DESCRIPTION

Figure 3A:
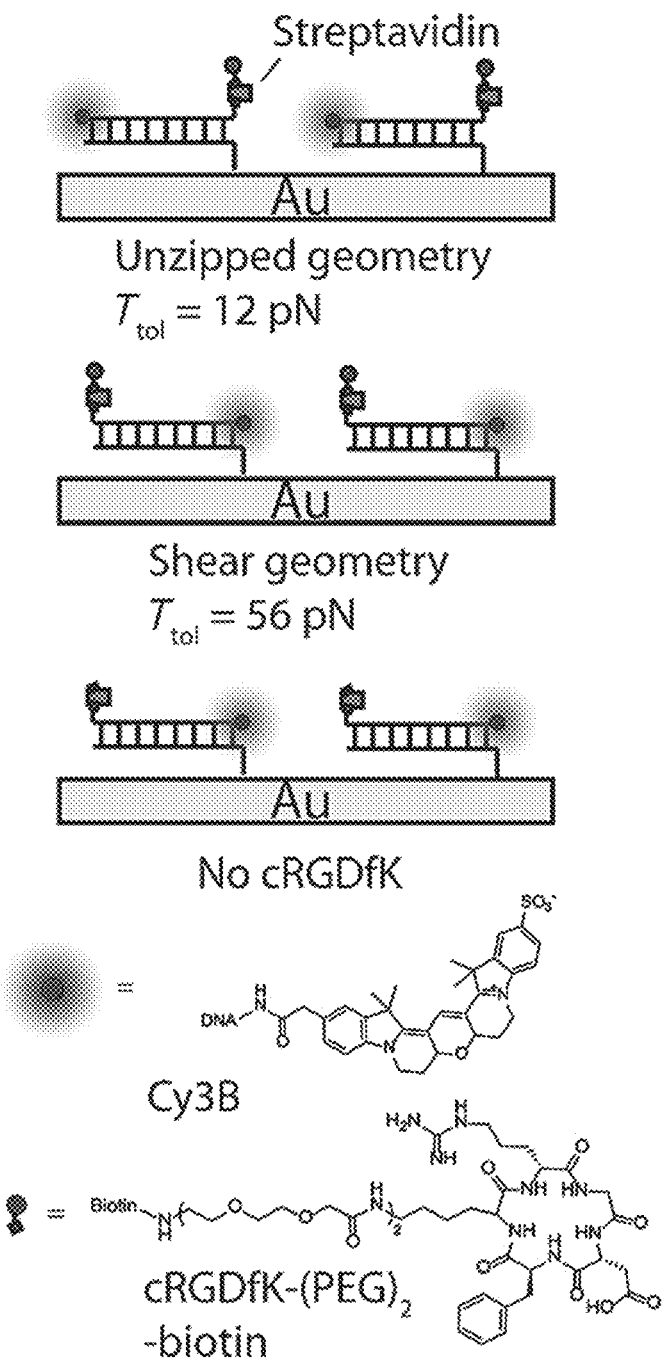
FIG. 3A shows a schematic of mechanically labile duplexes used to study integrin-mediated forces.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the terms "ligand" and "receptor" refer to specific bonding partners and are not meant to be limited to naturally occurring biomolecules. In most embodiments, disclosed herein the ligand and receptor can be interchanged even though a "ligand" typically refers to a binding partner with a lower molecular weight. Binding partners are considered specific if they have attractive forces to each other that are in excesses of a similar category of molecules. Binding partners are not covalently attached; but, instead are attracted to each other through, hydrogen bonding, hydrophobic Van der Waals forces, and/or ionic interactions. It is contemplated that the receptor may be a truncated version of a naturally occurring molecule. Contemplated receptors include naturally occurring receptors, antibodies, proteins, and antibody mimetics. In certain embodiments, a ligand may be a peptide or molecule with a molecular weight of greater than 200.

"Hydrogen binding partners" refer to bonding partners wherein hydrogen bonding arrangements are the major attractive forces. Double-stranded nucleic acids are held together by hydrogen bonds between complementary nucleobases. The term "hybridize" is not intended to be limited to completely matching pairs as altering the number of mismatches are contemplated and can be used to lower the binding strength.

As used herein, the term "nucleic acid" is intended to mean a ribonucleic or deoxyribonucleic acid or analog thereof, including a nucleic acid analyte presented in any context; for example, a probe, target or primer. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base. Exemplary non-native bases that can be included in a nucleic acid, whether having a native backbone or analog structure, include, without limitation, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

A non-native base used in a nucleic acid can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which basepairs with cytosine, adenine or uracil. Alternatively, or additionally, oligonucleotides, nucleotides or nucleosides including the above-described non-native bases can further include reversible blocking groups on the 2', 3' or 4' hydroxyl of the sugar moiety.

The term "nucleobase polymer" refers to a polymer comprising nitrogen containing aromatic or heterocyclic bases that bind to naturally occurring nucleic acids through hydrogen bonding otherwise known as base pairing. A typical nucleobase polymer is a nucleic acid, RNA, DNA, or chemically modified form thereof. A nucleic acid may be single or double stranded or both, e.g., they may contain overhangs. Nucleobase polymers may contain naturally occurring or synthetically modified bases and backbones. In certain embodiments, a nucleobase polymer need not be entirely complementary, e.g., may contain one or more insertions, deletions, or be in a hairpin structure provided that there is sufficient selective binding. With regard to the nucleobases, it is contemplated that the term encompasses isobases, otherwise known as modified bases, e.g., are isoelectronic or have other substitutes configured to mimic naturally occurring hydrogen bonding base-pairs, e.g., within any of the sequences herein U may be substituted for T, or T may be substituted for U. Examples of nucleotides with modified adenosine or guanosine include, but are not limited to, hypoxanthine, xanthine, 7-methylguanine. Examples of nucleotides with modified cytidine, thymidine, or uridine include 5,6-dihydrouracil, 5-methylcytosine, 5-hydroxymethylcytosine. Contemplated isobases include 2'-deoxy-5-methylisocytidine (iC) and 2'-deoxy-isoguanosine (iG) (see U.S. Pat. Nos. 6,001,983; 6,037,120; 6,617,106; and 6,977,161). In another embodiment, a removable base (such as uracil or 8-oxoguanine) is contemplated so that treatment by uracil-DNA glycosylase (UDG) or formamidopyrimidine-DNA glycosylase (FPG), can lead to cleavage and degradation of unwanted sequences.

In order to prevent breakdown nucleic acids may be chemically modified, e.g., within the sugar backbone or on the 5' or 3' ends. As such, in certain embodiments, nucleobase polymers disclosed herein may contain monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, P-(2-(hydroxymethyl)morpholino)-N,N-dimethylphosphonamidate, morpholin-2-ylmethanol, (2-(hydroxymethyl)morpholino) (piperazin-1-yl) phosphinate, or peptide nucleic acids or combinations thereof.

The term "nucleobase polymer that hybridizes" refers to a molecule capable of hybridizing to a single-stranded nucleic acid target. The nucleobase polymer may be single stranded nucleic acid or analog containing a sufficiently small number of mismatches, additions, or deletions as long as the probe retains the ability to bind to the target. The nucleobase polymer may be the single stranded tail of a double stranded nucleic acid. The nucleobase polymer may be a part of a loop structure or single stranded tail of a hairpin structure.

In certain embodiments, a nucleobase polymer has a sequence of more than 7, 8, 9, 10, 11, 12, 13, 14, 15 or more nucleotides or nucleobases or continuous nucleotide nucleobases that is the reverse complement of a binding partner. In certain embodiments, the nucleobase polymer is less than 100, 50, or 25 nucleobases or base pairs. In certain embodiments, the nucleobase polymer is more than three nucleotides optionally less than seven, or more than four nucleotides optionally less than seven, or more than five nucleotides and optionally less than seven.

A nucleobase polymer may be created by human intervention through chemical synthesis or expression through the use of a recombinant vector and typically amplification, e.g., PCR. The synthetic, non-naturally occurring nucleobase polymer is typically less than about one hundred nucleotides or less than fifty nucleotides.

Alternatively, the nucleic acid molecules can be synthesized separately and joined together post-synthetically, for example, by ligation or by hybridization following synthesis and/or deprotection.

Nucleic acids can also be assembled from two distinct nucleic acid strands or fragments wherein one fragment includes the sense region and the second fragment includes the antisense region of the RNA molecule.

The nucleic acid molecules can be modified extensively to enhance stability by modification with nuclease resistant groups, for example, 2'-amino, 2'-O-allyl, 2'-fluoro, 2'-O-methyl, 2'-H). Constructs can be purified by gel electrophoresis using general methods or can be purified by high pressure liquid chromatography and re-suspended in water.

Chemically synthesizing nucleic acid molecules with modifications (base, sugar and/or phosphate) can prevent their degradation by serum ribonucleases, which can increase their potency. See e.g., U.S. Pat. Nos. 5,652,094, 5,334,711, and 6,300,074. All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

In one embodiment, nucleic acid molecules include one or more (e.g., about 1, 2, 3, 4, 5, 6, 7, 8, 9, 10, or more) G-clamp nucleotides. A G-clamp is a tricyclic aminoethylphenoxazine 2'-deoxycytidine or analogue. See Lin &. Matteucci, J Am Chem Soc, 1998, 120, 8531-8532; Flanagan, et al., Proc Nat Acad Sci USA, 1999, 96, 3513-3518; and Maier, et al., Biochemistry, 2002, 41, 1323-1327. A single G-clamp analog substitution within an oligonucleotide can result in substantially enhanced helical thermal stability and mismatch discrimination when hybridized to complementary oligonucleotides. The inclusion of such nucleotides in nucleic acid molecules results in both enhanced affinity and specificity to nucleic acid targets, complementary sequences, or template strands.

In another embodiment, nucleic acid molecules include one or more (e.g., about 1, 2, 3, 4, 5, 6, 7, 8, 9, 10, or more) LNA "locked nucleic acid" nucleotides e.g. backbone monomers of 1-(hydroxymethyl)-2,5-dioxabicyclo[2.2.1]heptan-7-ol, (see for example U.S. Pat. Nos. 6,639,059, 6,670,461, 7,053,207).

In another aspect, nucleobase polymers comprises one or more 5' and/or a 3'-cap structure, for example on only the sense strand, the antisense strand, or both strands.

A "cap structure" refers to chemical modifications, which have been incorporated at either terminus of the nucleobase polymers. See, for example, Adamic et al., U.S. Pat. No. 5,998,203. These terminal modifications protect the nucleic acid molecule from exonuclease degradation. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide;

modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (for more details see Beaucage and Iyer, 1993, Tetrahedron 49, 1925).

In one embodiment, the disclosure features modified nucleobase polymer, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkyl silyl, substitutions.

As used herein, the term "linking" refers to attaching moieties by using covalent bonds, typically using a "linking group." A "linking group" refers to any variety of molecular arrangements that can be used to bridge to molecular moieties together. An example formula may be —$R_m$— wherein R is selected individually and independently at each occurrence as: —$CR_mR_m$—, —$CHR_m$—, —CH—, —C—, —$CH_2$—, —$C(OH)R_m$, —C(OH)(OH)—, —C(OH)H, —$C(Hal)R_m$—, —C(Hal)(Hal)-, —C(Hal)H—, —$C(N_3)R_m$—, —$C(CN)R_m$—, —C(CN)(CN)—, —C(CN)H—, —$C(N_3)(N_3)$—, —$C(N_3)$H—, —O—, —S—, —N—, —NH—, —$NR_m$—, —(C=O)—, —(C=NH)—, —(C=S)—, —(C=$CH_2$)—, which may contain single, double, or triple bonds individually and independently between the R groups. If an R is branched with an $R_m$ it may be terminated with a group such as —$CH_3$, —H, —CH=$CH_2$, —CCH, —OH, —SH, —$NH_2$, —$N_3$, —CN, or -Hal, or two branched Rs may form a cyclic structure. It is contemplated that in certain instances, the total Rs or "m" may be less than 100 or 50 or 25 or 10. Examples of linking groups in include bridging alkyl groups and alkoxyalkyl groups.

Mechanically Induced Catalytic Amplification Reaction for Readout of Receptor-Mediated Cellular Forces Disclosed herein is a mechanically induced catalytic amplification reaction (MCR) to readout the signal associate with piconewton forces applied by cell surface receptors. The strategy utilizes a blocked initiator of an enzymatic reaction that is exposed through the action of mechanical forces. Given the fidelity and sensitivity of PCR, DNA amplification is exemplified as a readout for MCR.

As illustrated in FIG. 1, a DNA duplex modified with a ligand is surface immobilized. When cells are plated on the surface, adhesion receptors engage their ligands and apply mechanical forces (Freceptor). Receptor-mediated tension exceeding the $T_{tol}$ exposes the blocked primer for amplification.

MCR using isothermal amplification was used instead of PCR to minimize background arising from thermal denaturation of the blocked primer. For amplification, an 81-mer linear DNA template is hybridized and circularized by T4 ligase. Subsequently, the primer strand is replicated with isothermal rolling circle amplification (RCA). Under optimal conditions, the RCA reaction replicates a circular template thousands of times, generating a long tandem repeat of DNA. The repetitive amplified product is then visualized by fluorescence in situ hybridization (FISH), an established technique for sensitive nucleic acid detection with high specificity. Quantification of the product can be achieved by direct surface imaging, or by release of fluorescent oligonucleotides followed by high-throughput plate reader measurements. In principle, each mechanical rupturing event is transduced and amplified into hundreds of fluorescent oligonucleotides.

Immobilization imposes a steric constraint on polymerases. The efficiency and selectivity of RCA was quantified on a surface. 5'-Thiol modified primers with a T10 spacer were immobilized onto gold films and amplified, as described in FIG. 1. Surface imaging of hybridized FISH probes in the amplified samples revealed a fluorescent monolayer with a 15.7 plus or minus 4.9% coefficient of variation (CV) in intensity (FIG. 2A), which is likely because of heterogeneous efficiency of polymerization on the surface. In contrast, the non-amplified samples showed a 4.9 plus or minus 0.3% CV, demonstrating that the hybridization of the complement to the primer strand is relatively more homogeneous. The fluorescence signal in the amplified primer samples showed a 102 plus or minus 4-fold increase compared to non-amplified samples (FIG. 2B). Solution amplification shows approximately 1000-fold replication of the circular template, as determined by gel electrophoresis indicating that surface confinement inhibits polymerase activity and reduces the overall amplification efficiency. The roughly 100-fold enhancement in signal represents the maximum amplification of a mechanically triggered dehybridization event into a chemical output.

MCR was used to detect forces mediated by integrins, which are a family of heterodimeric cell surface receptors that mediate cell adhesion and migration. Integrins physically bridge the cellular cytoskeleton with the extracellular matrix, and accordingly experience piconewton forces. Integrin-mediated denaturation of immobilized DNA duplexes were quantified. 5'-Cy3B, 3'-biotin labeled complement was hybridized to the primer to generate a fluorescently labelled duplex (FIG. 3A). Biotin-streptavidin binding was used to present the cyclic Arg-Gly-Asp-d-Phe-Lys (SEQ ID NO: 1) (cRGDfK) peptide, a high-affinity ligand for integrin receptors.

Figure 3B:
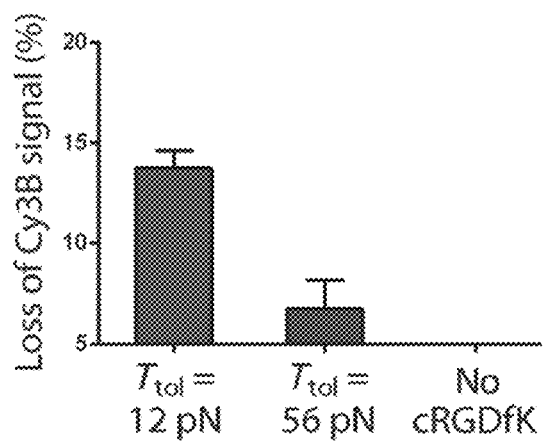
FIG. 3B shows a plot quantifying loss of Cy3B fluorescence, which indicates mechanical DNA denaturation.

In this geometry, mechanical forces denature the duplex in an unzipping mode with a predicted $T_{tol}$=12 pN. An identical primer sequence hybridized to a complement with 3'-Cy3B, 5'-biotin, leads to denaturation in a shearing mode with a predicted $T_{tol}$=56 pN. Note that the surface presents chemically identical probes with differing mechanical tolerance. After plating NIH/3T3 fibroblast cells on these surfaces for 1 h, we observed a loss in fluorescence that colocalized with the cell footprint, as indicated by reflection interference contrast microscopy. Minimal loss in fluorescence was observed when the cRGDfK adhesion peptide was withheld. The decrease in Cy3B fluorescence under individual cells (FIG. 3B) was quantified. Greater fraction of the $T_{tol}$=12 pN duplexes were denatured (13.7 plus or minus 0.9% decrease in fluorescence) compared to that of the $T_{tol}$=56 pN duplex (6.5 plus or minus 0.45% decrease in fluorescence). The data shows differential mechanical denaturation of DNA duplexes, with a two-fold difference in DNA loss when comparing the 12 pN to 56 pN duplexes.

To catalytically amplify exposed primers, 100 000 cells were plated to the 12 and 56 pN surfaces (surface area=68.58 mm$^2$) and allowed them to spread for 1 h. This cell density corresponds to a full monolayer (680 mm$^2$ available per cell, assuming each cell can spread ca. 900 mm$^2$). MCR was performed and the fluorescently tagged probes were imaged by epifluorescence microscopy. A significant fluorescence signal was observed on the surface. Therefore, primer amplification can readily be used to detect integrin-driven denaturation of blocked primers. Note that MCR was performed in standard conditions (Tris-OAc (20 mm), KOAc (50 mm), Mg(OAc)$_2$ (10 mm), BSA (100 mgmL$^{-1}$), pH 7.9), as media compatible with cells (such as DMEM, PBS, and HEPES) inhibit polymerase activity needed for MCR. Therefore, cells are absent during readout, likely because of multiple washing and incubation steps in MCR buffer.

Figure 4A:
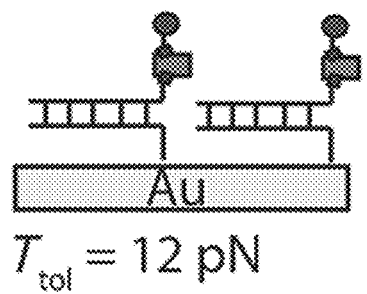
FIG. 4A shows a schematic a duplexes with $T_{tol}$=12 pN for MCR to report integrin forces.
Figure 4B:
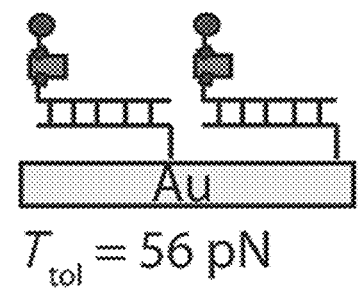
FIG. 4B shows a schematic a duplexes with $T_{tol}$=56 pN.
Figure 4C:
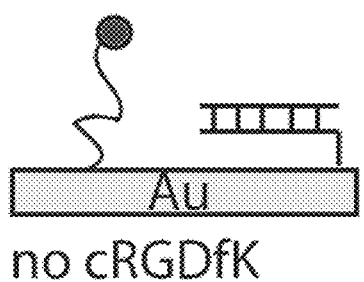
FIG. 4C shows a schematic of duplexes lacking the cRGDfK peptide.
Figure 4D:
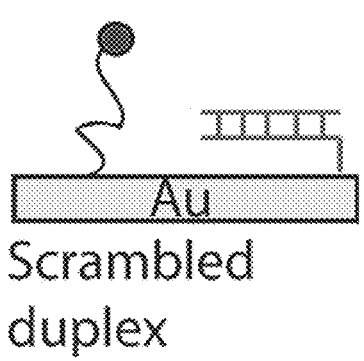
FIG. 4D shows a schematic of scrambled duplexes.

Controls using duplexes lacking cRGDfK (FIG. 4C) and scrambled duplexes non-complementary to the template (FIG. 4D) confirmed the specificity of MCR. In these controls, the DNA surface was doped with 10% (by incubation concentration) single-stranded DNA labeled with cRGDfK to mediate cell adhesion. The cell density was nearly identical on all the tested surfaces indicating that the density of cRGDfK ligands was sufficient to trigger cell adhesion prior to MCR readout. All controls showed low signal, approximately 150-fold lower than that generated by the 12 pN surface (FIGS. 4C and D). The background signal is likely to arise from amplification of single stranded primers exposed because of spontaneous dissociation of DNA duplexes. Confirming this result, an approximately 3% loss of fluorescently labeled DNA duplexes was found from the surface when incubated in cell imaging media for 3 hrs at 37° C.

Figure 4E:
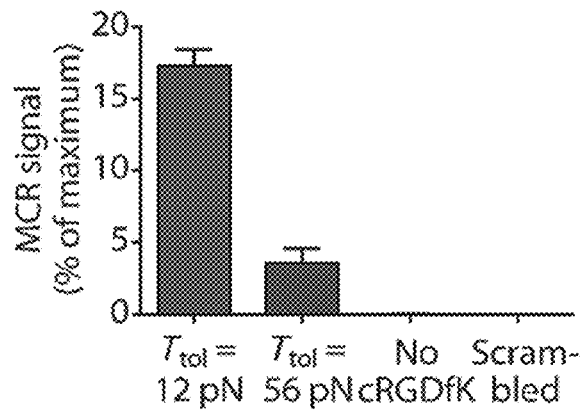
FIG. 4E shows a bar graph showing the average MCR signal from 30 different images from three independent samples.
Figure 4F:
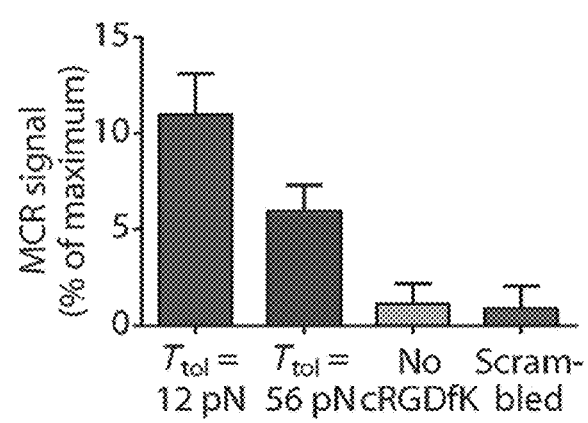
FIG. 4F shows a bar graph showing the intensity of the eluent following release of FISH probes from the surfaces and detected by a microplate reader.

The bar graphs in FIGS. 4E and F show the results of quantifying the MCR signal using imaging-based, and plate reader-based readouts, respectively. For plate reader-based readout, the bound FISH probes were released by dehybridization with nanopure water, and then transferred to a 96-well plate where fluorescence was quantified. The fluorescence intensity was normalized to the maximum MCR signal obtained from a monolayer of primer (ca. 3.5×10$^4$ primers per mm$^2$) prepared in the same batch. The differences between image based and plate-reader based readouts are likely because of differential levels of background and sensitivity; the image based readout is likely to be more sensitive. The 12 pN duplex showed a roughly five-fold and 2.7-fold greater signal than that of the 56 pN duplex in FIGS. 4E and 4F, respectively, consistent with the mechanically induced dehybridization data in FIG. 3.

Figure 5A:
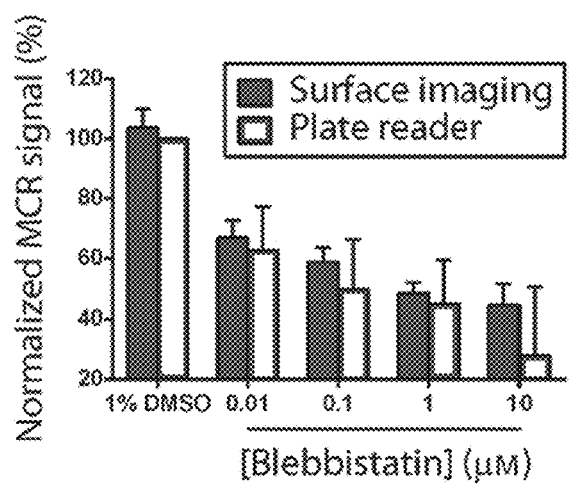
FIG. 5A shows data on MCR signal for NIH/3T3 cells treated with increasing concentrations of blebbistatin (0.01-10 mm).

Suitability of the MCR amplification reaction in drug screening by measuring the effect of a drug on integrin mechanics rather than cell viability was demonstrated. The non-muscle myosin II inhibitor blebbistatin, which diminishes myosin contractility and thus reduces forces transmitted by focal adhesions, was investigated. NIH/3T3 cells were pretreated with a range of blebbistatin concentrations (10 nm-10 mm) for 15 min. The cells onto the surface were incubated with the 12 pN duplexes for 1 h, which was then followed by MCR readout. Brightfield imaging indicated that cells become more rounded with increasing drug dose. This observation is confirmed by F-actin staining, which showed more disorganized and shorter actin filaments at the highest blebbistatin doses. Correspondingly, the MCR signal displayed a dose-dependent relationship, where the highest blebbistatin concentrations generated the lowest MCR signal (FIG. 5A). The MCR signal is a direct readout of integrin tension, measuring the dose-dependent dissipation of actomyosin contractile forces.

Figure 5B:
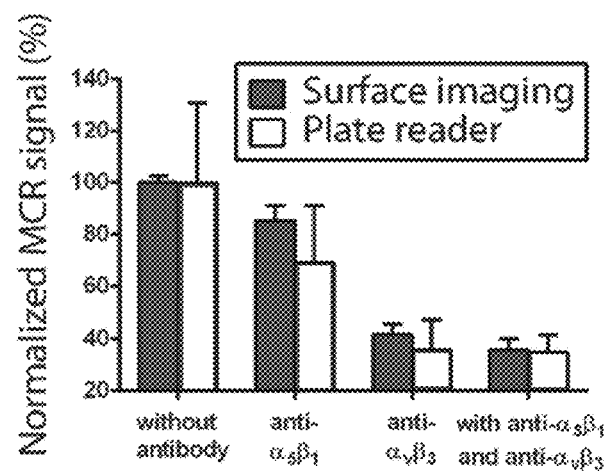
FIG. 5B shows data in a bar chart quantifying MCR signal in the presence of anti-alpha 5 beta 1, anti-alpha v beta 3, or both antibodies, relative to the sample without antibodies.
Figure 6A:
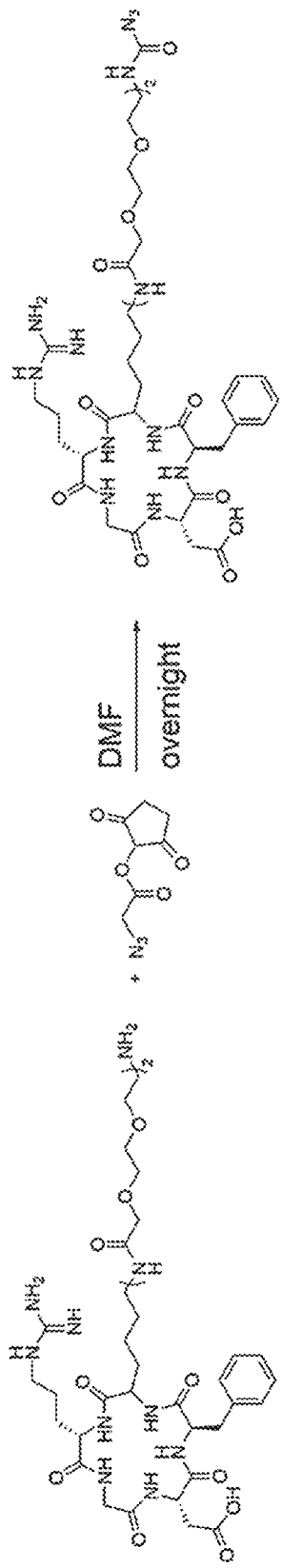
FIG. 6A illustrates c((RGDfK(PEG-PEG))-azide conjugate (1).
Figure 6B:
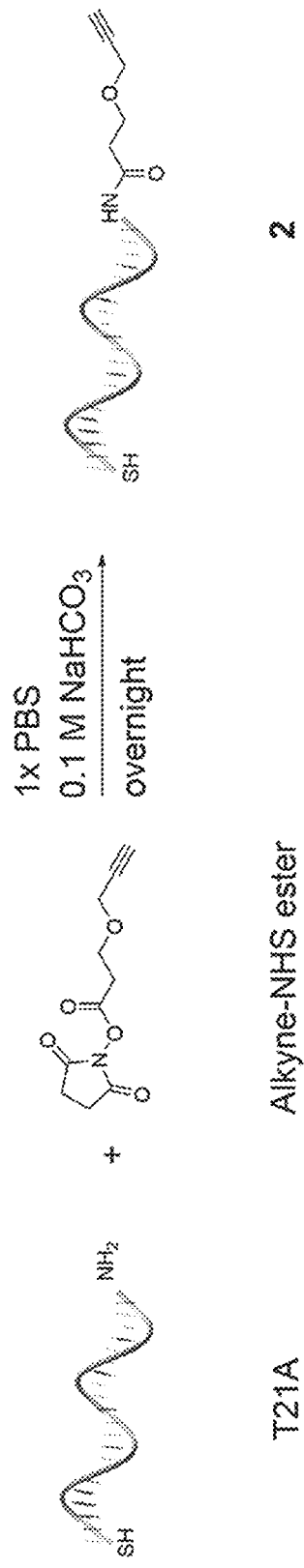
FIG. 6B illustrates the preparation of T21A-alkyne (2).
Figure 6C:
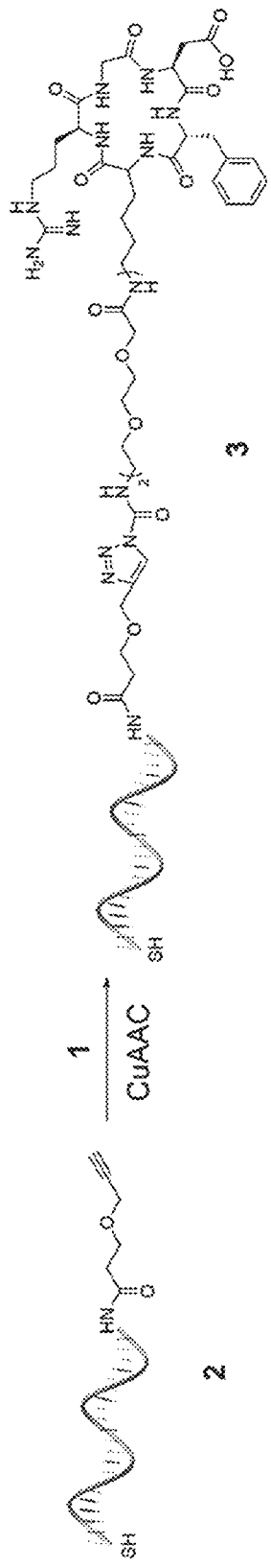
FIG. 6C illustrates the preparation of T21A-cRGDfK (3).
Figure 7A:
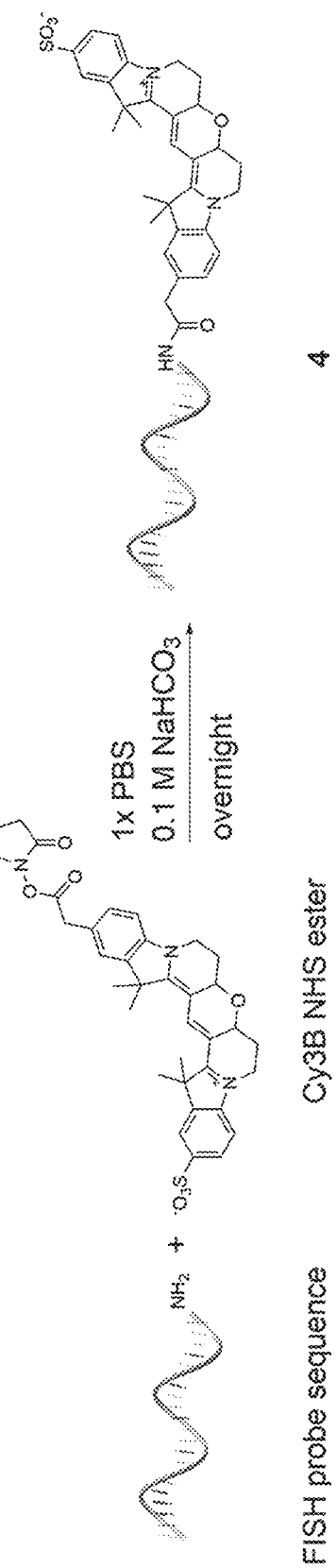
FIG. 7A illustrates the preparation of Cy3B-FISH probe (4).
Figure 7B:
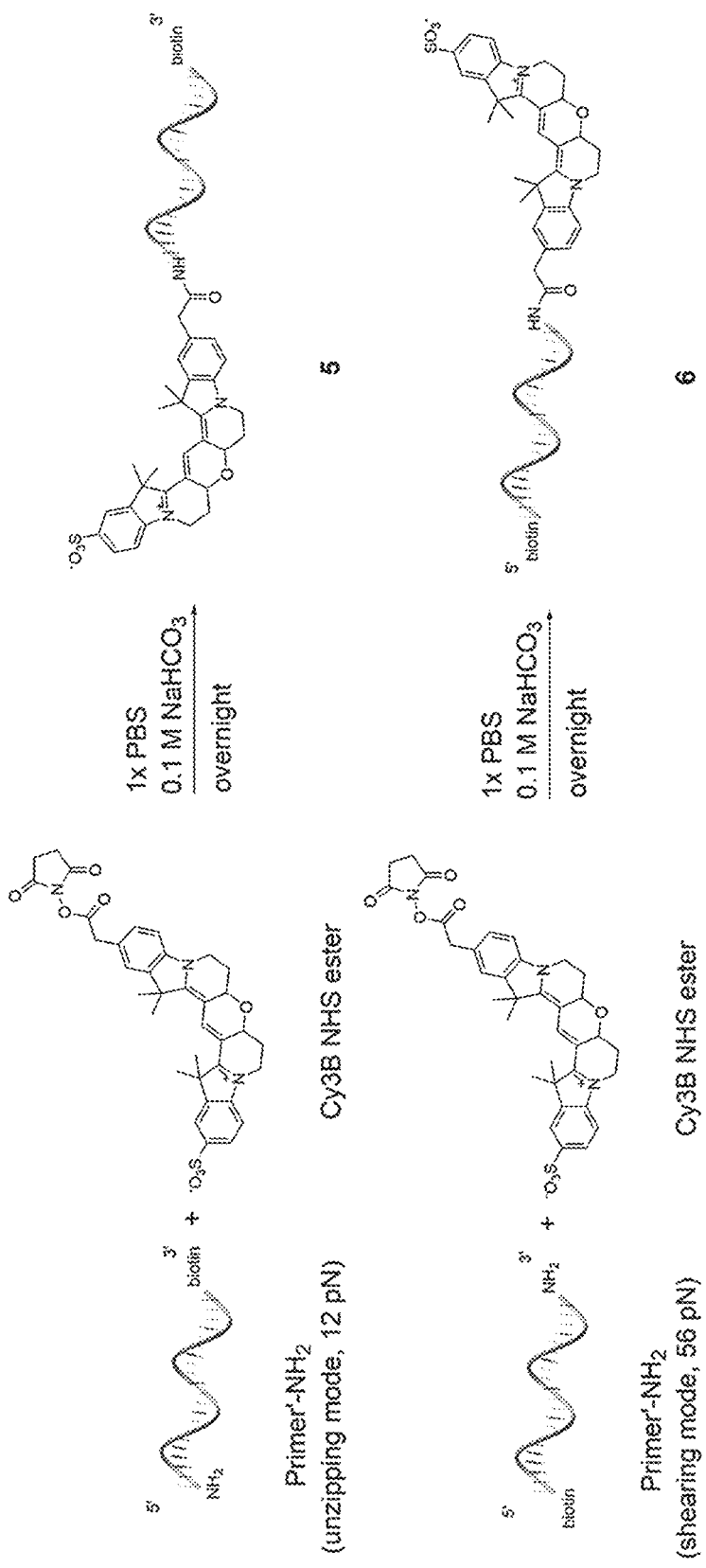
FIG. 7B illustrates the preparation of primer'-Cy3B [unzipping, 12 pN (5)] and primer'-Cy3B [shearing, 56 pN (6)].

To further highlight the utility of MCR, the MCR signal was measured on the 12 pN duplex surfaces in response to inhibiting different integrin subtypes. The two major integrin subtypes mediating adhesion of NIH/3T3 fibroblasts are alpha v beta 3 and alpha 5 beta 1 that display divergent cellular functions. In surface-based imaging, anti-alpha v beta 3 antibody treatment reduced the MCR signal by 59.6 plus or minus 4.1%, while anti-alpha 5 beta 1 antibody treatment reduced the MCR signal by 14.6 plus or minus 5.6% (FIG. 5B). Incubation with both antibodies led to the greatest reduction in MCR signal (64.4 plus or minus 4.3%). Plate reader measurement showed a similar trend. This is an example of screening drugs that target cellular mechanics using a catalytic amplification assay.

EXAMPLES

Solution-Based Rolling Circle Amplification (RCA)

Rolling circle amplification—1 pmol of the circular template and the tether strand were mixed in 1×Phi29 DNA polymerase reaction buffer containing 250 µM dNTPs and 1 U/mL Phi29 polymerase. The reaction was allowed to react at 37° C. from 0 to 90 min. Nucleic acid sequence are provided in the table below.

| Name | Sequence (From 5' to 3')$^a$ |
|---|---|
| Circular template | /5Phos/CCGTGTCACGGAATGGTTACTTGCACAGCC AGCAGCCTCACGGAATTCACGGAATGGTTACTTGCAC AGCGTGTCGTGCCT (SEQ ID NO: 2) |
| FISH probe sequence | /5AmMC6/TCACGGAATGGTTACTTGCACAGC (SEQ ID NO: 3) |
| primer | /5ThiolMC6-D/T$_{10}$CACAGCACGGAGGCACGACAC (SEQ ID NO: 4) |
| T21A | /5ThiolMC6D/TTTGCTGGGCTACGTGGCGCTCTT/3AmMO/ (SEQ ID NO: 5) |
| primer' (unzipping mode, 12 pN) | GTGTCGTGCCTCCGTGCTGTG/3Bio/ (SEQ ID NO: 6) |
| primer' (shearing mode, 56 pN) | /5BiosG/GTGTCGTGCCTCCGTGCTGTG (SEQ ID NO: 7) |
| primer'-NH$_2$ (unzipping, 12 pN) | /5AmMC6/GTGTCGTGCCTCCGTGCTGTG/3Bio/ (SEQ ID NO: 8) |
| primer'-NH$_2$ (shearing, 56 pN) | /5BiosG/GTGTCGTGCCTCCGTGCTGTG/3AmMO/ (SEQ ID NO: 9) |

Fabrication of Gold Thin Films

75×25 mm glass slides (Cat. no: 10812, ibidi, Verona, Wis.) were sonicated in a 1:1 mixture of nanopure water and isopropanol for 30 min, and allowed to dry at ambient conditions. Metal deposition was performed by thermal evaporation using an in-house thermal evaporation chamber (Department of Physics, Emory University) with a quartz crystal microbalance (QCM) thickness monitor. Thermal evaporation was conducted at 5×10-7 Pa. A thin 1.5 nm chromium adhesion layer was evaporated on the glass slide to promote gold adhesion. Subsequently, a 4 nm gold layer was deposited on the chromium coated glass slide. The system was allowed to cool to room temperature before removing the gold slides from the chamber to prevent carbon contamination. The thin gold films were stored in sealed petri dishes and cleaned with absolute ethanol before use.

Preparation of Oligonucleotide Modified Gold Film

Figure 8A:
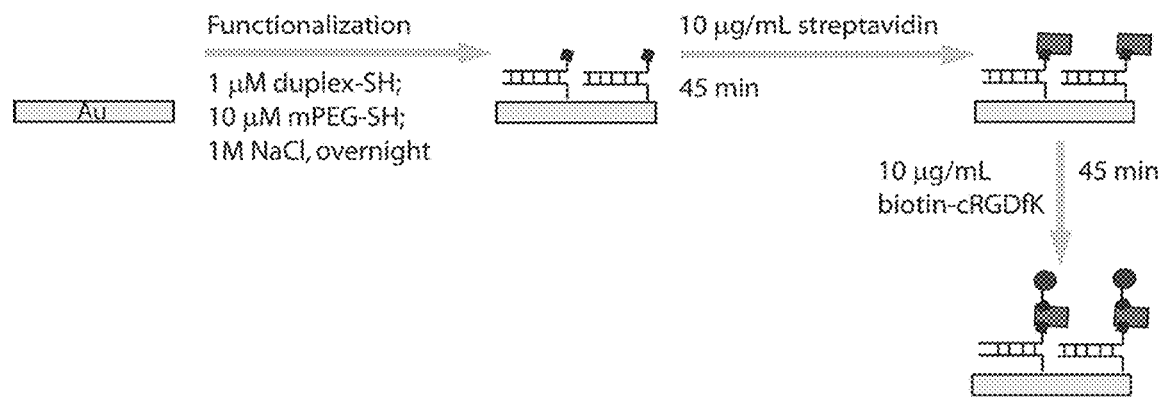
FIG. 8A illustrates the fabrication of thin gold film decorated with mechanically sensitive duplexes.

Duplex-modified gold films (FIG. 8A): 6.67 µM of primer and primer' were hybridized in 1×PBS by annealing to 95° C. for 5 min and the mixture was allowed to cool to room temperature. A 6-channel µ-Slide (ibidi, Verona, Wis.) was mounted on the thin gold film to create 6-well flow chambers with a channel volume of ~40 μL. The hybridized duplexes were dissolved in 1 M sodium chloride solution (Final concentration of duplexes=1 μM) and were allowed to incubate on a thin gold film overnight at 4° C. with 10 μM of HS—(CH2)11-(OCH2CH2)6-OCH3 passivating polyethylene glycol. Excess DNA and PEG were removed with three washes of 0.1×SSC (1.5 mM sodium citrate, 15 mM NaCl, pH=7.0). Afterwards, 10 μg/mL of streptavidin was added and incubated with the surfaces for 45 min. The surfaces were then washed with 0.1×SSC and subsequently 10 μg/mL of cRGDfK-biotin ligand was added and allowed to bind to the streptavidin modified duplexes for 45 min. Unbound ligand was washed away with 0.1×SSC and the surfaces were used within the same day of preparation.

ssDNA-modified gold films: 1 μM of primer was dissolved in 1 M sodium chloride solution and allowed to incubate on a thin gold film overnight at 4° C. with 10 μM of HS—(CH2)11-(OCH2CH2)6-OCH3 passivating polyethylene glycol. Excess DNA and PEG were removed with three washes of 0.1×SSC and used within the same day.

Quantification of the Density of Surface-Immobilized DNA

A monolayer of dsDNA was prepared according to the abovementioned protocol. The duplex DNA was de-hybridized with three washes of Nanopure water and the eluents were collected and qualified by the Oligreen™ assay in 96 well plate format.

Preparation of Glass Surfaces Labelled with cRGDfK

Figure 8B:
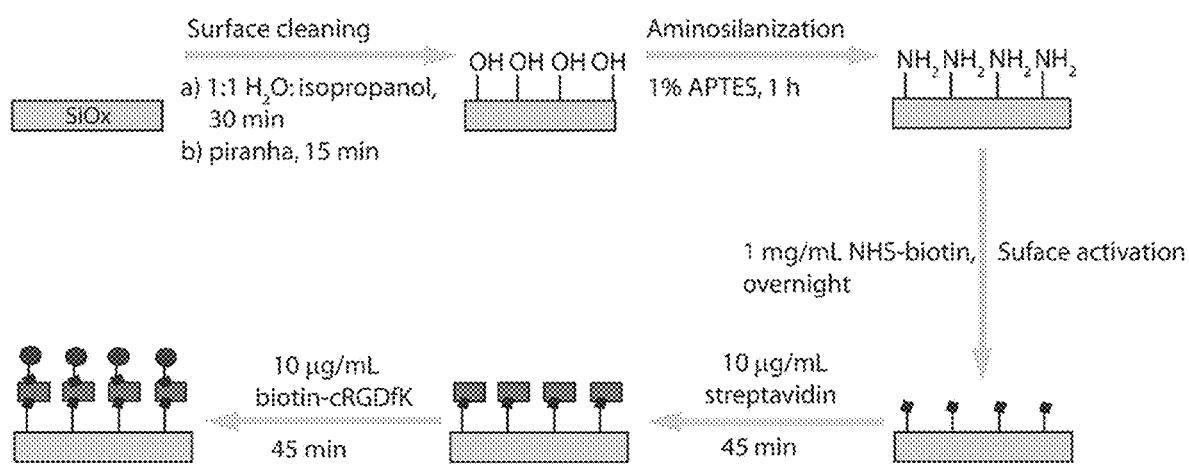
FIG. 8B illustrates fabrication of glass surface labelled with cRGDfK.

The surfaces were prepared according to FIG. 8B. In brief, 75×25 mm glass slides were sonicated in a 1:1 mixture of Nanopure water and isopropanol for 30 min, and etched in piranha solution (Caution: Piranha can be explosive if mixed with organic solvent!) for 15 min. The slides were then washed six times in Nanopure water and further washed in ethanol three times. Slides were then transferred to a beaker containing 1% APTES in ethanol for 1 h. Slides were extensively washed with ethanol and dried in an oven set to 80° C. A 6 channel μ-Slide was then mounted to APTES functionalized glass slides to create 6 well flow chambers. 1 mg/mL biotin-NHS solution dissolved in ethanol was then introduced and allowed to incubate with the surface overnight. Surfaces were then washed extensively with Nanopure water and 1×PBS. 10 μg/mL of streptavidin was added to the chambers and incubated for 45 min. Excess streptavidin was washed out with 1×PBS. Then 10 μg/mL of biotin-cRGDfK ligand was added and incubated for 45 min. Surfaces were washed with 1×PBS and used within the same day.

Preparation of Gold Nanoparticles Decorated with dsDNA

Figure 8C:
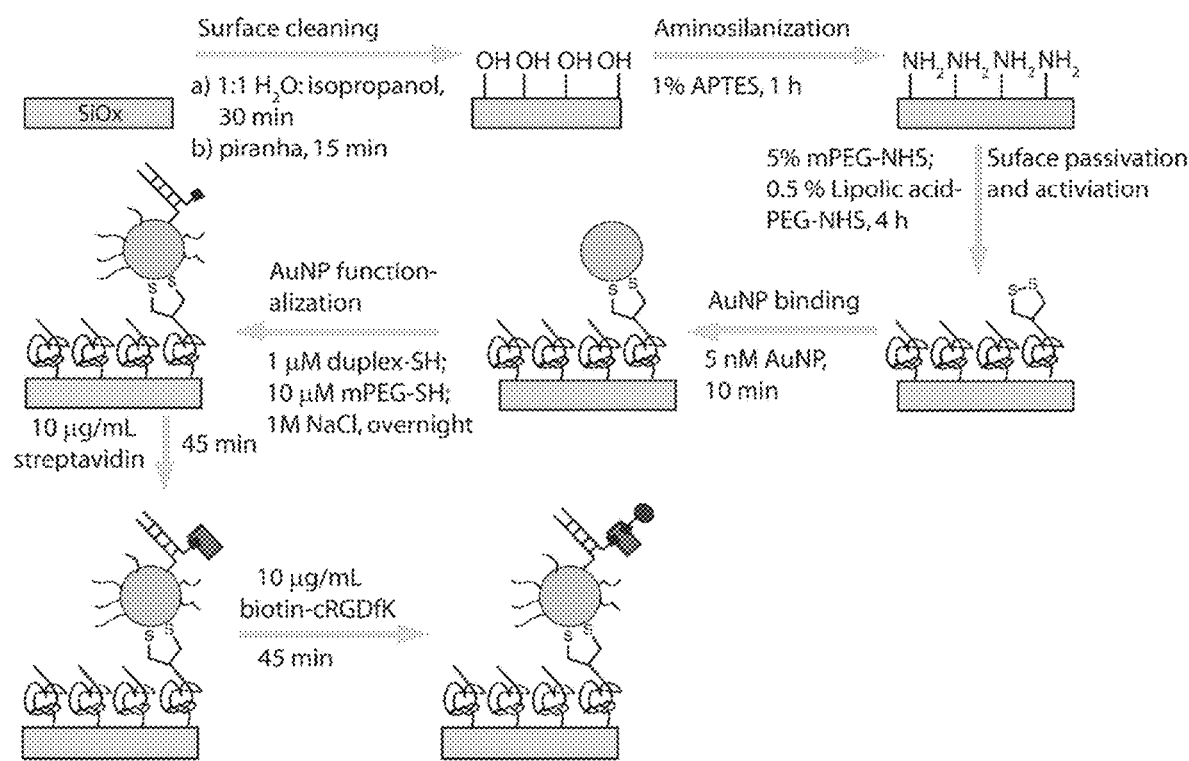
FIG. 8C illustrates fabrication of gold nanoparticle surface decorated with mechanically sensitive duplexes.
Figure 9A:
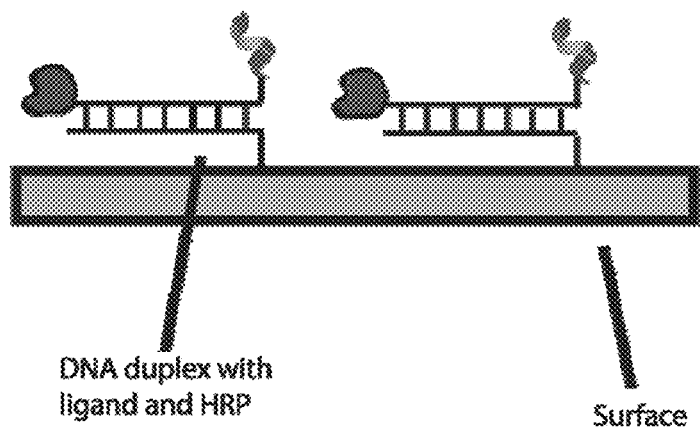
FIG. 9A illustrates that devices disclosed herein can also be used to tag the previously unidentified proteins surrounding mechanically active receptors. In this scenario, the DNA duplex contains a ligand on one end (right) and a catalytic enzyme (e.g. HRP, on the left) on the other end will be used.
Figure 9B:
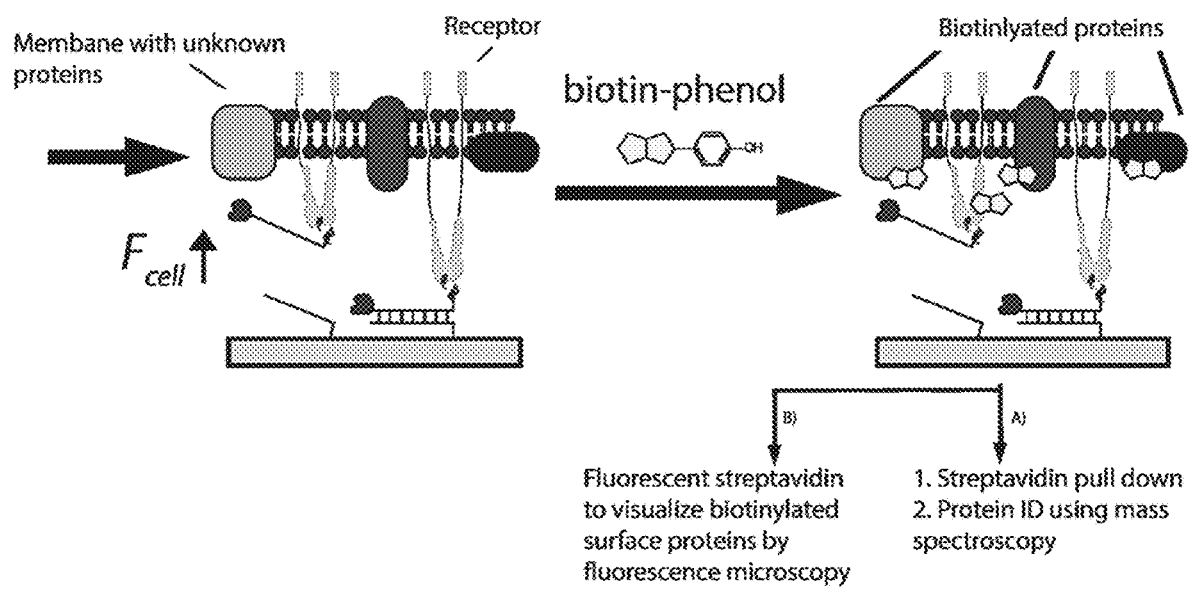
FIG. 9B illustrates when the receptor exerts forces and denatures the DNA duplex, the upper strand containing ligand and HRP will ligate to the mechanically active receptor, and bring the HRP in close proximity to the lipid membrane of the cell. An enzymatic biotinylation approach can be used to sample the recruitment of proteins surrounding the mechanically active receptors. These proteins can be visualized using fluorescently labelled streptavidin under fluorescence microscopy, and be identified using MS/MS techniques. See Lam et al., Directed evolution of APEX2 for electron microscopy and proximity labeling. Nature Methods. 2015; 12(1):51-4 and Hung et al., Spatially resolved proteomic mapping in living cells with the engineered peroxidase APEX2. Nature Protocols. 2016; 11(3):456-75.

As illustrated in FIG. 8C, 75×25 mm glass slides were sonicated in a 1:1 mixture of Nanopure water and isopropanol for 30 min, and etched in piranha solution for 15 min. The slides were then washed six times in Nanopure water and further washed in ethanol three times. Slides were then transferred to a beaker containing 1% APTES in ethanol for 1 h. Subsequently, slides were extensively washed with ethanol and dried in an oven set to 80° C. A 6 channel μ-Slide was then mounted to APTES functionalized glass slides to create 6 well flow chambers. Then 5% mPEG-NHS and 0.5% lipoic acid-NHS (w/v) in 0.1 M NaHCO3 were added and incubated for 4 h. Surfaces were washed extensively with Nanopure water and then 5 nM AuNP solution was introduced and incubated for 10 min. Surfaces were washed extensively with Nanopure water and then dried with nitrogen. The hybridized duplexes were dissolved in 1 M sodium chloride solution and were allowed to incubate overnight at 4° C. with 10 μM of HS—(CH2)11-(OCH2CH2)6-OCH3 passivating polyethylene glycol. Excess DNA and PEG were removed with three washes of 0.1×SSC. Afterwards, 10 μg/mL of streptavidin was added and incubated for 45 min. The surfaces were then washed with 0.1×SSC and subsequently 10 μM of cRGDfK-biotin ligand was added and allowed to bind to the streptavidin modified duplexes for 45 min. Unbound ligand was washed away with 0.1×SSC and the surfaces were used within the same day of preparation.

Mechanically-Induced Catalytic Amplification Reaction (MCR)

Cells were incubated with the cRGDfK-labelled duplex surfaces in DMEM for 1 h to promote cell adhesion. Surfaces were then washed with 0.1×SSC. Subsequently, surfaces were incubated in 1× CutSmart® buffer (20 mM Tris-acetate, 10 mM Mg(OAc)$_2$, 50 mM KOAc, 100 μg/mL BSA, pH 7.9) with 100 nM circular template and 1 U/μL T4 ligase at 37° C. for 2 h to ensure complete ligation. Then, 250 μM dNTPs and 0.1 U/μL Phi 29 polymerase were added to the solutions and mixed well. The surfaces were incubated at 37° C. for 90 min to allow for rolling circle amplification. The chambers were washed with 0.1×TNT/0.1% SDS (15 mM NaCl, 1 mM Tris-HCl, 0.005% Tween-20, 0.1% SDS, pH=8.0) and dried. Finally, the surface was incubated with 100 nM Cy3B-FISH probe in hybridization buffer (0.5 M NaCl, 20 mM Tris-HCl, 20 mM EDTA, and 0.01% Tween, pH=7.4) at 37° C. for 30 min, rinsed with three washes of 0.1×TNT/0.1% SDS and subjected to fluorescence imaging.

Dose-Dependent Inhibition of Integrin Mediated Tension Quantified by MCR

Serial dilutions of blebbistatin (10 μM to 10 nM) were added to 50 μL DMEM containing 100,000 cells/mL, respectively, and the drug treated cells were incubated in 1.5 mL Eppendorf tube for 15 min. The drug treated cells were added to the duplex coated ($T_{tol}$=12 pN) thin gold film assembled with a flow chamber and incubated at 37° C. for 1 h. Surfaces were then washed with 0.1×SSC and MCR was performed following the previously described procedures.

Antibody Blocking Assay

As illustrated in FIG. 5B, NIH/3T3 cells were co-incubated with 10 μg/mL of monoclonal antibodies selective for integrin α5β1 (anti-α5β1 antibody, Millipore) or αvβ3 (anti-αvβ3 antibody, R&D systems) on gold surfaces fabricated with cRGDfK-labelled duplexes ($T_{tol}$=12 pN) for 1 h. Surfaces were then washed with 0.1×SSC. MCR was performed following the previously described procedures. Experiments were performed on DNA duplex immobilized onto gold nanoparticles rather than gold films. This required a slightly different protocol. Immobilizing DNA duplexes on gold nanoparticles afforded improved signal by increasing the optical transparency of the substrate.

The invention claimed is:

1. A method of identifying an adhesion receptor of cells binding to a ligand, the method comprising;
   incubating 1) a device comprising:
   a) a surface,
   b) a first strand of a nucleobase polymer linked to an area of the surface,
   c) a second strand of the nucleobase polymer configured to hybridize with the first strand of the nucleobase polymer wherein the first strand of the nucleobase polymer and the second strand of the nucleobase polymer form a duplex, and
   d) a ligand linked to the second strand of the nucleobase polymer; and
   2) cells containing an adhesion receptor in a condition for a time period to promote adhesion of the cells such that the adhesion receptor of the cells engages the ligand of the second strand of the nucleobase polymer on the duplex and applies a mechanical force, which is a receptor-mediated tension, to the duplex,
   the first strand of the nucleobase polymer no longer hybridizes to the second strand of the nucleobase polymer, and the first strand of the nucleobase polymer becomes a single stranded in the area of the surface, if the adhesion receptor of the cells binds to the ligand of the second strand of the nucleobase polymer and the receptor-mediated tension exceeds a total force needed to denature the duplex;
   adding a circular DNA template to the surface after the incubating step and performing an amplification reaction such that an amplified DNA is produced by amplifying the circular DNA template using the first strand of the nucleobase polymer as a primer if the adhesion receptor of the cells binds to the ligand of the second strand of the nucleobase polymer and the receptor-mediated tension exceeds a total force needed to denature the duplex; and
   identifying the adhesion receptor of the cells binding to the ligand by detecting the amplified DNA.

2. The method of claim 1, wherein the ligand comprises a polysaccharide, peptide, glycopeptide, or steroid.

3. The method of claim 1, wherein the receptor comprises a polypeptide having ten or more amino acids.

4. The method of claim 1, wherein the device is a surface comprising gold nanoparticles wherein the first stand of the nucleobase polymer is linked to the gold nanoparticles.

5. The method of claim 1 wherein said amplifying the circular DNA template comprises isothermally amplifying the circular DNA template.

6. The method of claim 1, wherein said detecting the amplified DNA comprises hybridizing the amplified DNA with a fluorescent probe.

* * * * *

UNITED STATES PATENT AND TRADEMARK OFFICE
CERTIFICATE OF CORRECTION

| | | |
|---|---|---|
| PATENT NO. | : 10,900,069 B2 | Page 1 of 1 |
| APPLICATION NO. | : 15/456024 | |
| DATED | : January 26, 2021 | |
| INVENTOR(S) | : Salaita et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 377 days.

Signed and Sealed this
Fourteenth Day of February, 2023

Katherine Kelly Vidal
*Director of the United States Patent and Trademark Office*

SEQUENCE LISTING

<160> NUMBER OF SEQ ID NOS: 9

<210> SEQ ID NO 1

```
<211> LENGTH: 5
<212> TYPE: PRT
<213> ORGANISM: Artificial Sequence
<220> FEATURE:
<223> OTHER INFORMATION: Synthetic

<400> SEQUENCE: 1

Arg Gly Asp Phe Lys
1               5

<210> SEQ ID NO 2
<211> LENGTH: 81
<212> TYPE: DNA
<213> ORGANISM: Artificial Sequence
<220> FEATURE:
<223> OTHER INFORMATION: Synthetic

<400> SEQUENCE: 2
ccgtgtcacg gaatggttac ttgcacagcc agcagcctca cggaattcac ggaatggtta      60
cttgcacagc gtgtcgtgcc t                                                81

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
tcacggaatg gttacttgca cagc                                             24

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
cacagcacgg aggcacgaca c                                                21

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
tttgctgggc tacgtggcgc tctt                                             24

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
gtgtcgtgcc tccgtgctgt g                                                21

<210> SEQ ID NO 7
<211> LENGTH: 21
<212> TYPE: DNA
<213> ORGANISM: Artificial Sequence
<220> FEATURE:
```

```
<223> OTHER INFORMATION: Synthetic

<400> SEQUENCE: 7
gtgtcgtgcc tccgtgctgt g                                          21

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
gtgtcgtgcc tccgtgctgt g                                          21

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
gtgtcgtgcc tccgtgctgt g                                          21
```